United States Patent
Colister et al.

(10) Patent No.: US 12,387,840 B2
(45) Date of Patent: **\*Aug. 12, 2025**

(54) REMOTE VIEW PLAYBACK TOOL

(71) Applicant: Talis Clinical LLC, Streetsboro, OH (US)

(72) Inventors: Gary Colister, Hudson, OH (US); Giuseppe Saracino, Gainsville, FL (US); William Murphy, Aurora, OH (US); Harish Lecamwasam, Scottsdale, AZ (US)

(73) Assignee: TALIS CLINICAL LLC, Streetsboro, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,303

(22) Filed: Mar. 17, 2021

(65) Prior Publication Data
US 2021/0202082 A1 Jul. 1, 2021

Related U.S. Application Data

(63) Continuation-in-part of application No. 16/239,077, filed on Jan. 3, 2019, now abandoned.
(Continued)

(51) Int. Cl.
*G16H 40/20* (2018.01)
*H04N 21/2387* (2011.01)
*H04N 21/472* (2011.01)

(52) U.S. Cl.
CPC ......... *G16H 40/20* (2018.01); *H04N 21/2387* (2013.01); *H04N 21/47202* (2013.01); *H04N 21/47217* (2013.01)

(58) Field of Classification Search
CPC ........ G16H 50/20; G16H 80/00; G16H 10/60; G16H 40/67; A61B 5/7275; A61B 5/0022;
(Continued)

(56) References Cited

U.S. PATENT DOCUMENTS 5,954,666 A 9/1999 Snell
6,229,536 B1 5/2001 Alexander et al.
(Continued)

FOREIGN PATENT DOCUMENTS

EP 3839960 6/2021
JP 2004-533662 A 11/2004
(Continued)

OTHER PUBLICATIONS

Canadian Intellectual Property Office, Office Action Issued in Application No. 3,087,566, Sep. 3, 2024, 5 pages.

*Primary Examiner* — Daniel W Parcher
(74) *Attorney, Agent, or Firm* — McCoy Russell LLP

(57) ABSTRACT

A remote view playback system for use by medical practitioners to improve patient outcomes, including a patient database and data storage engine including means for collecting and storing data from any number of electronic devices and instructions for transmitting data to any number of electronic devices and for storing data associated with the patient records and/or data to be stored as quality data; a communication hub for collecting, agnostically, data from any number of electronic devices and instructions for transmitting data to any number of electronic devices, and for storing data associated with the patient records to be stored as quality data, and providing access to all data, so that data from multiple disparate sources can be acquired and consolidated within a unified view; optionally, at least one monitoring station; and a user interface rules engine to collect, store and process data in real time, compose views that organize data, notify end-users based on execution steps defined by end-users, display an organized view of data within a timeline of events, change, for end-users, or augment the execution steps, provide notifications at the same time the end-user is reviewing data, and apply one or more rules to the data selected from assessment data from each
(Continued)

monitored patient to determine whether a rule for that monitor has been violated or whether best practice rules established by a health care provider are being adhered to as expected.

9 Claims, 13 Drawing Sheets

Related U.S. Application Data

(60) Provisional application No. 62/613,218, filed on Jan. 3, 2018.

(58) Field of Classification Search
CPC ... A61B 5/7282; A61B 5/7465; G06F 3/0482; G06F 3/0484; G06F 16/22; G06F 16/215
See application file for complete search history.

(56) References Cited

U.S. PATENT DOCUMENTS

| | | |
|---|---|---|
| 6,364,834 B1 | 4/2002 | Reuss et al. |
| 6,553,436 B2 | 4/2003 | Ando et al. |
| 6,559,868 B2 | 5/2003 | Alexander et al. |
| 7,315,825 B2 | 1/2008 | Rosenfeld |
| 7,467,093 B1 | 12/2008 | Newton et al. |
| 8,000,937 B2 | 8/2011 | Zeng et al. |
| 8,149,131 B2 | 4/2012 | Blomquist |
| 8,229,760 B2 | 7/2012 | Hasan et al. |
| 8,291,337 B2 | 10/2012 | Gannin et al. |
| 8,310,336 B2 | 11/2012 | Muhsin et al. |
| 8,553,036 B2 | 10/2013 | Taylor et al. |
| 8,660,860 B2 | 2/2014 | Wehba et al. |
| 8,674,837 B2 | 3/2014 | Gilham et al. |
| 8,730,243 B2 | 5/2014 | Wenholz et al. |
| 8,892,171 B2 | 11/2014 | Ross et al. |
| 8,990,722 B2 | 3/2015 | Gannon et al. |
| 9,095,274 B2 | 8/2015 | Fein et al. |
| 9,179,852 B2 | 11/2015 | Audet et al. |
| 9,393,366 B2 | 7/2016 | Gannon et al. |
| 9,400,874 B2 | 7/2016 | Powell et al. |
| 9,927,943 B2 | 3/2018 | Gannon et al. |
| 10,255,408 B2 | 4/2019 | Blomquist |
| 10,354,751 B1 | 7/2019 | McNair |
| 10,657,222 B2 | 5/2020 | Chan et al. |
| 11,030,872 B2 | 6/2021 | Chan et al. |
| 11,031,129 B2 | 6/2021 | Zaleski |
| 2002/0143320 A1* | 10/2002 | Levin ............... G06K 17/00 977/932 |
| 2004/0044775 A1* | 3/2004 | Takano ............... H04L 67/56 709/227 |
| 2004/0054294 A1 | 3/2004 | Ramseth |
| 2005/0159666 A1 | 7/2005 | Pearce et al. |
| 2005/0171815 A1 | 8/2005 | Vanderveen |
| 2007/0179806 A1 | 8/2007 | Knowlton et al. |
| 2008/0097914 A1 | 4/2008 | Dicks et al. |
| 2008/0316045 A1 | 12/2008 | Sriharto et al. |
| 2009/0070054 A1* | 3/2009 | Zeng ............... A61B 5/339 702/67 |
| 2011/0227739 A1 | 9/2011 | Gillham et al. |
| 2012/0035957 A1 | 2/2012 | Hanz et al. |
| 2012/0075103 A1* | 3/2012 | Powell ............... G16H 15/00 340/573.1 |
| 2012/0278099 A1* | 11/2012 | Kelly ............... G16H 10/60 705/2 |
| 2014/0046674 A1 | 2/2014 | Rosenfeld et al. |
| 2014/0142963 A1 | 5/2014 | Hill et al. |
| 2014/0222446 A1 | 8/2014 | Ash et al. |
| 2014/0249855 A1 | 9/2014 | Moore |
| 2014/0266787 A1 | 9/2014 | Tran |
| 2014/0350966 A1 | 11/2014 | Khatana et al. |
| 2015/0025329 A1 | 1/2015 | Amarasingham et al. |
| 2016/0117446 A1* | 4/2016 | Hussam ............... G16H 80/00 705/3 |
| 2016/0246943 A1 | 8/2016 | Lake et al. |
| 2017/0140108 A1 | 5/2017 | Lee et al. |
| 2017/0372037 A1 | 12/2017 | Muecke et al. |
| 2020/0035366 A1 | 1/2020 | Gummireddy et al. |
| 2020/0227148 A1 | 7/2020 | Cohen et al. |
| 2020/0359913 A1 | 11/2020 | Ghodrati et al. |
| 2020/0394334 A1 | 12/2020 | Bulut et al. |
| 2021/0065889 A1 | 3/2021 | Page |
| 2021/0077035 A1 | 3/2021 | Kayser et al. |
| 2021/0141786 A1 | 5/2021 | Gubau i Forné et al. |
| 2021/0151145 A1 | 5/2021 | Dunn et al. |
| 2021/0151178 A1 | 5/2021 | Singh et al. |
| 2021/0202086 A1 | 7/2021 | Cherdak |
| 2021/0225505 A1 | 7/2021 | Khare et al. |
| 2021/0233628 A1 | 7/2021 | Rentas et al. |

FOREIGN PATENT DOCUMENTS

| | | |
|---|---|---|
| JP | 2012-529351 | 11/2012 |
| JP | 2015-530901 | 10/2015 |
| JP | 2016-519806 A | 7/2016 |
| WO | 2017/218579 | 12/2017 |
| WO | 2021067485 | 4/2021 |
| WO | 2021002847 | 7/2021 |

\* cited by examiner

REMOTE VIEW PLAYBACK TOOL

CROSS REFERENCE TO RELATED APPLICATIONS

This application is a continuation-in-part of, and claims the benefit of, U.S. patent application Ser. No. 16/239,077, filed Jan. 3, 2019, which is entitled "Remote View Playback Tool," and is incorporated herein by reference.

BACKGROUND OF THE INVENTION

The present invention is directed to a remote view playback tool, which facilitates, for example, converting patient vital signs into waveforms to facilitate remote monitoring of patients and improve decisions regarding patient care.

Medical devices actively monitoring patient vital signs often display waveforms. The waveforms and corresponding numeric values are used to make decisions regarding the patient care at the point of care. However, today there are limited means to collect and store these waves forms in patient records. When saved the saved information appears as a screen shot. This significantly limits the effectiveness of telemedicine interaction with remote specialists and its use during after the fact assessments of never events.

To fully support telemedicine and after the fact assessments of specific patient care procedures, there is a real need to be able to have access to the entire waveform data collected during the patient care. This supports the assessment of the patient responses to various potential contributors during the patient care. Without the ability to select specific times during the patient care to assess the entire history of the patient care, the assessments are limited to an incomplete picture of the whole story. To effectively review the data, especially data from multiple sources, it needs to be viewed in a time synchronized format that allows the user to see the time with an ability to detect potential cause and effect results. In this way, the data can be reviewed as singular data sources. If the data, including patient care interaction and patient results represented by vital signs and lab results, were time synchronized and overlapped on the same screen the user would have the ability to make more informed decisions.

Today telemedicine is used to support remote ICU bunkers. The intensivist monitoring these ICU patients have access to a video feed that shows the actual medical device active monitoring screens. This approach provides only the current vital signs. There is no ability to review earlier details to fully assess the potential contributions to the current patient condition. Remote view provides a means to store vital signs including waveforms in the patient record. These records may be less than a second behind the active patient monitor screens. Once stored the remote view allows the remote practitioner to easily move back and forth through the records to fully assess the needs of the patient and when appropriate provide guidance to the practitioner.

Telemedicine should not be limited to remote ICU bunkers or Command centers. Utilizing the enhanced data discussed above by providing the data remotely via mobile devices and other access points, as well as ICU bunkers and command centers, significantly increase the potential use of telemedicine.

Today there is no easy-way for a physician to have access to the most current condition of their patients remotely. Remote view provides the physician or other authorized practitioners to readily see the patient condition in real time, as well as the ability to review the patient's condition leading up to the current status. The alternative today is attempting to contact someone on duty and have them review the patient's condition over the phone, creating opportunities for miscommunications.

Remote view supports telemedicine by providing the remote practitioner with real time access the patient's record and ability to review all vital signs, patient care activities and patient response to the treatment leading up to the current condition. This provides for a more complete understanding of the patient condition. An example of this is as Anesthesiologist supervising multiple CRNA's. Remote view provides the supervisor to review the facts regarding a specific patient while walking to the OR to assist the CRNA. Thus, reducing the time required to review the patient status with the CRNA prior to taking the appropriate actions to address the situation.

Effective telemedicine requires the ability to assess the impact of all patient interactions and the patient response to those interactions. However, even electronic patient records are limited to a series of snap shots in time during patient care. The snap shots routinely do not adequately provide a means to assess the patient response to the interactions. Therefore, the determination of correlation between any specific patient interaction is often based on opinions based on prior experience, but not based on scientifically supported facts.

The limitation placed on telemedicine is the content of the patient care record. This is especially true with paper records and/or electronic medical records that focus on procedural and billing documentation. The patient records limitations include the information included in the patient record does not provide enough details to clearly assess the relevant information available to the practitioner at the time of the event or prior to the event. The limitations could include, for example, the numeric values of patient vital signs, the waveform information, the specific timelines for interactions, and access to data not contained in the patient record Numeric values of patient vital signs displayed on medical device screens are not collected frequently enough to properly assess the patient response to a specific interaction with the patient or advanced knowledge of patient condition. Waveform information displayed on medical devices may not be part of the patient record. Even when present, the content is a series of snap shots at prescribed intervals. The snap shots do not routinely provide the details needed. Specific timelines show all patient interactions with patient vital signs before and after each patient interaction. Any ability to access any past data is limited if it not contained in the patient record. Because, for the most part, the current systems do not collect the data, it is not available for subsequent review.

Medical devices monitoring patient vital signs often display waveforms. The waveforms and corresponding numeric values can be critical to make decisions regarding the patient care. However, today there are no or very limited means to collect and store these waves forms in patient records. When saved the saved information appears as a screen shot. This significantly limits the effectiveness of telemedicine interaction with remote specialists and its use during after the fact assessments of never events. While real time video is reviewed remotely, there is no ability to review the recent history previously shown on the active patient monitor, or review all data provided by the medical device during the case.

To fully support telemedicine, there is a real need to be able to have access to the entire collected during the patient care, including the waveform data. This supports the assessment of the patient responses to various potential contributors during the patient care. Without the ability to select specific times during the patient care to assess the entire history of the patient care, the assessments are limited to an incomplete picture of the whole story.

SUMMARY OF THE INVENTION

The present invention is directed to a remote view playback tool or system and method for medical practitioners to improve patient outcomes.

The system includes a patient database and data storage engine including a data storage_means for collecting and storing data from any number of electronic devices including medical devices and instructions for transmitting data to any number of electronic and for storing data associated with the patient records and/or data to be stored as quality data; a communication hub for collecting, agnostically, data from any number of electronic devices and instructions for transmitting data to any number of electronic devices, and for storing data associated with the patient records to be stored as quality data, and providing access to all data, so that data from multiple disparate sources can be acquired and consolidated within a unified view; optionally, a monitoring station; and a user interface rules engine to collect, store and process data in real time, compose views that organize data, notify end-users based on execution steps defined by end-users, display an organized view of data within a timeline of events, change, for end-users, or augment the execution steps, provide notifications at the same time the end-user is reviewing data, and apply one or more rules to the data selected from assessment data from each monitored patient to determine whether a rule for that monitor has been violated or whether best practice rules established by a health care provider are being adhered to as expected.

The user rules engine provides the user with the ability to select any point in time during the patient treatment to review the details collected regarding the treatment, before, after or at the selected time, create guidance rules to identify cases as non-complying with the defined rules, and define who, when and how to communicate that cases meeting defined criteria are available for review, where the who are individual(s) evaluating the defined criteria without notification to anyone monitoring a current case, or including specific individuals monitoring the current case.

If the rule has been violated, an alert is sent to any identified location including individual mobile devices and monitoring stations and wherein rules for each monitored patient can be established and changed at said identified location for a patient as a patients' condition warrants, and an alert that a rule has been violated includes advice on treatment of the patient.

The tool of the present invention allows the remote access to real time patient records, including data not necessarily included in the EMR. The remote access may include data available to the attending practitioner from the medical device active patient monitors in addition to the EMR data which is a subset of the complete data set. The tool may be used to create guidance rules to identify cases identified as complying with the defined rules, to define who, when and how to communicate that cases meeting the defined criteria are available for review, in this case the who may be only the individual(s) evaluating the defined criteria without notification to anyone monitoring a current case, or including specific individuals monitoring the current case.

DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION OF THE INVENTION

Figure 1:
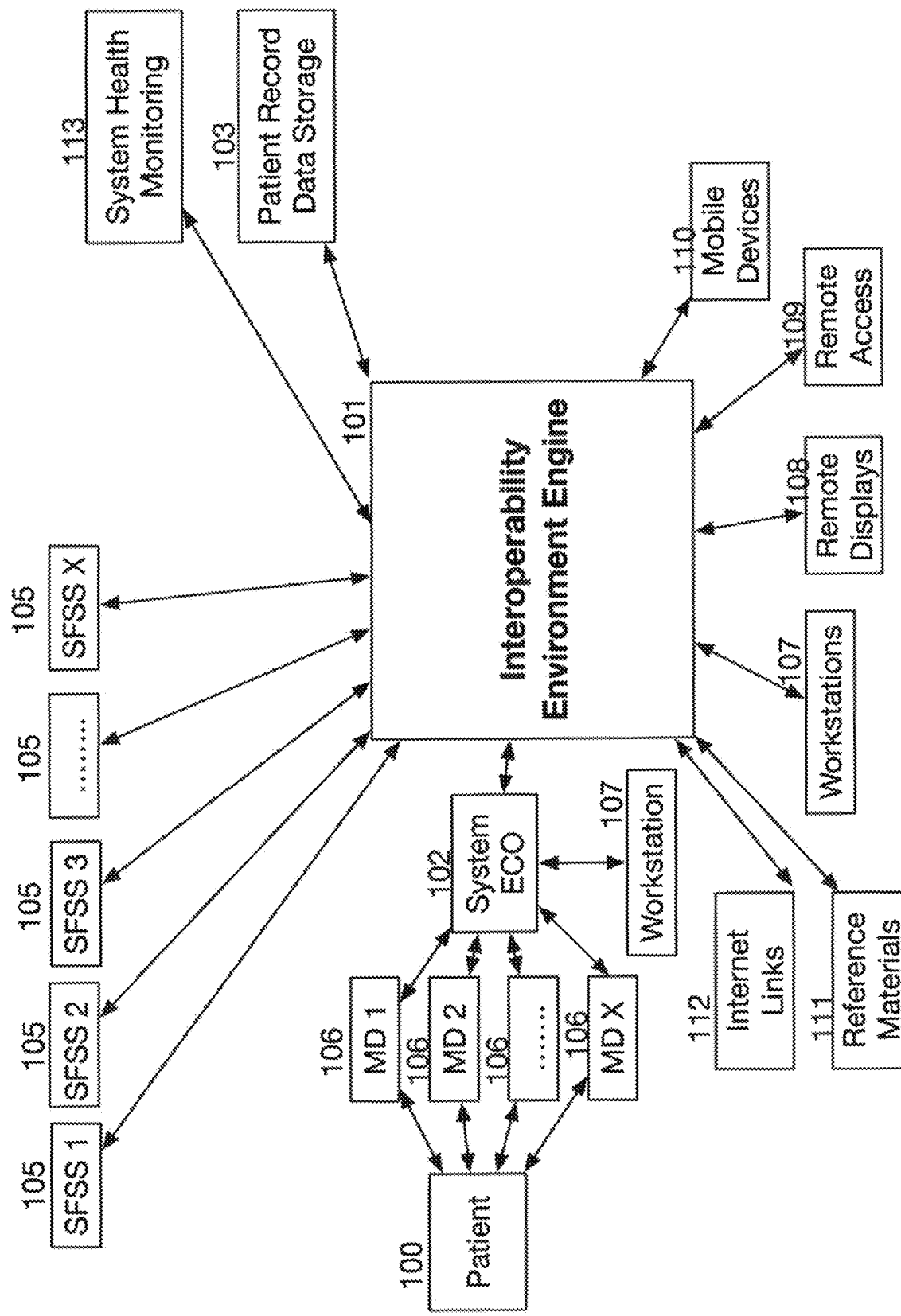
FIG. 1 is a flow diagram of a global view of the continuous improvement system used with the present invention.

The present invention is directed to a remote view playback tool or system, to facilitate remote monitoring and review of patient's medical data and trends and improve decisions regarding patient care. For example, the present invention facilitates converting patient vital signs into waveforms which can be stored with patent records and may be displayed and played for review.

The present invention is directed to a system and device for providing active care for a patient. The preset invention is robust enough that it can locate the application and data storage remote of the facility IT network and avoid the need for local data storage, which is limited to temporary data presence to protect against local network failures. All data, displayed for practitioner use, can be stored, analyzed and processed remote of the facility IT network. The presently claimed invention is not limited to any defined environment or type of facility. The present invention is a real time tool providing Clinical Decision Support to any number of medical practitioners based on the role assigned to the individual practitioner.

The present invention is directed to a remote view playback system for use by medical practitioners to improve patient outcomes, including a patient database and data storage engine including a data storage_means for collecting and storing data from any number of electronic devices and instructions for transmitting data to any number of electronic devices and for storing data associated with the patient records and/or data to be stored as quality data; a communication hub comprising instructions for collecting, agnostically, data from any number of electronic devices including medical devices and instructions for transmitting data to any number of electronic devices including medical devices, as well as instructions for storing data associated with the patient records and/or data to be stored as quality data, and providing access to all data, including continuous waveform data, collected during the treatment of the patient and quality data not included in any patient record storage location, whereby data from multiple disparate sources can be acquired and consolidated within a unified view; optionally, at least one monitoring station; a user interface rules engine including means to collect, store and process data in real time, compose views that organize data for end-users to consume, notify end-users based on execution steps defined by end-users, display an organized view of data within a timeline of events, change, for end-users, or augment the execution steps, provide notifications at the same time the end-user is reviewing data, and apply one or more rules to the data selected from assessment data from each monitored patient to determine whether a rule for that monitor has been violated or whether best practice rules established by a health care provider are being adhered to as expected.

The patient database will contain information concerning the medical condition, history, and status of each of the patients. The data storage engine will have a data storage-_means for collecting and storing data from any number of electronic devices including medical devices and instructions for transmitting data to any number of electronic devices including medical devices, as well as instructions for storing data associated with the patient records and/or data to be stored as quality data. The data storage engine is a software module on a programed computer that a database management system uses to create, read, and update data from a database. The engine tracks each data field based on a start date and end date of the parameter being collected. When combined with the engine time stamping and data collecting, the user interface rules engine is capable of supporting data analysis of individual parameters as well as interactions with other parameters. The data storage engine can be implemented advantageously in one or more computer programs that are known and executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

The user rules engine provides the user with the ability to select any point in time during the patient treatment to review the details collected regarding the treatment, before, after or at the selected time, create guidance rules to identify cases as non-complying with the defined rules, and define who, when and how to communicate that cases meeting defined criteria are available for review, where the who are individual(s) evaluating the defined criteria without notification to anyone monitoring a current case, or including specific individuals monitoring the current case; and When a rule has been violated, an alert is sent to any identified location including individual mobile devices and monitoring stations and wherein rules for each monitored patient can be established and changed at said identified location for a patient as a patients' condition warrants, and an alert that a rule has been violated includes advice on treatment of the patient.

The monitoring station includes monitoring equipment including instructions for monitoring data elements and for sending the monitored data elements via the telecommunications network, and including instructions for receiving monitored data elements from patients and accessing patient data elements indicative of a medical conditions associated with each of the patients, and the data can be reviewed remotely to make decisions about patient care.

The present invention can receive, store, transmit and display data including wave forms as provided by the medical device or other sources of truth. The wave forms are created by the medical devices or provided by other sources of truth. The calculation and creation of the wave form is not required.

The present invention provides a real time update of the details required for the practitioner to assess specific patient conditions and when appropriate, adjust scheduled activities as dictated by real time patient data including historical data, data collected from vital sign monitors and medical devices delivering patient treatment or data collected by practitioner selected time(s). The tool also allows the practitioner to select specific times to review patient response to interactions with the patient.

The present invention identifies a need to be able to review specific interactions with patient and patient response by being able to move back and forward in the patient record. To fully accomplish this there is a need to be able to replay the waveforms collected. The present invention is to a simple means to easily view remotely the historic waveform. Historic here is defined as any delay from the active patient monitoring. Therefore, using commonly accepted telemedicine practices, the active practitioners may consult with remote specialists if needed.

The remote screens support the ability to move back in time during the current patient care under review. The same screens may also be utilized to evaluate the case during formal reviews. These screens also include icons to show when specific patient interactions were performed.

The waveform data is collected directly from the medical devices. These waveforms are stored with the patient records. Once stored, the waveforms may be displayed and played on a remote device. With the ability to play the stored waveforms, the system is also able to play, replay, fast forward or fast reverse to identify the time periods of most interest to the medical practitioner reviewing these records.

The present invention allows for the acquisition of data from multiple disparate sources, consolidation of all information within a unified view, running process controls/workflows and delivering actionable insights to specific users in real time. The present system identifies which information is actionable based on user criteria, supplied by the user, and a decision support algorithm provided by management software. Actionable information can be presented with rich context compared to typical isolated ancillary systems. The information can be personalized to patient, clinical and/or admin user. Users can replay the timeline of events with all relevant information under a given context. Information can be added or deleted to sharpen context, to gain additional knowledge, or to immediately implement changes based on the review.

Figure 12:
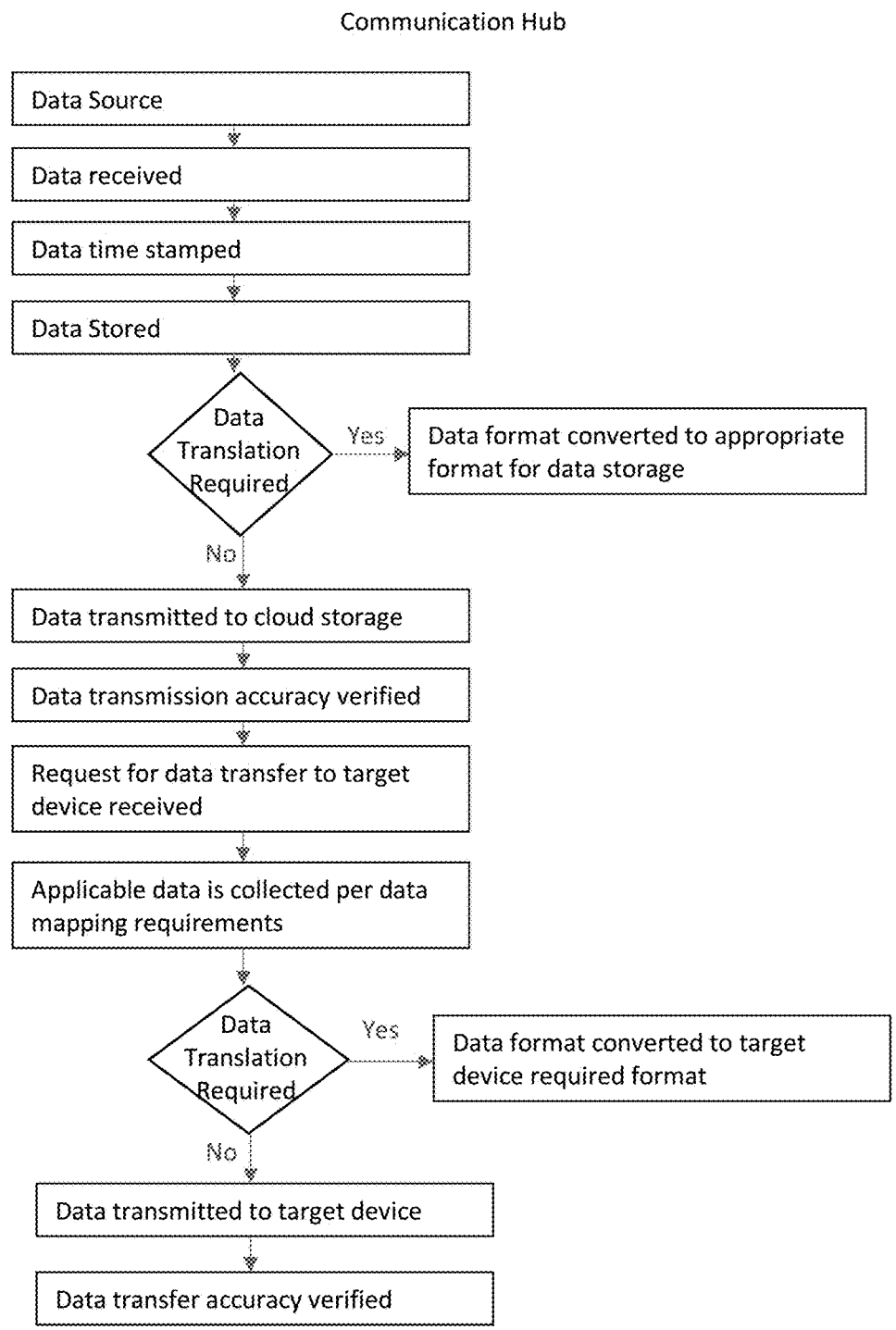
FIG. 12 is a flow diagram of the communications hub of the present invention.
Figure 13:
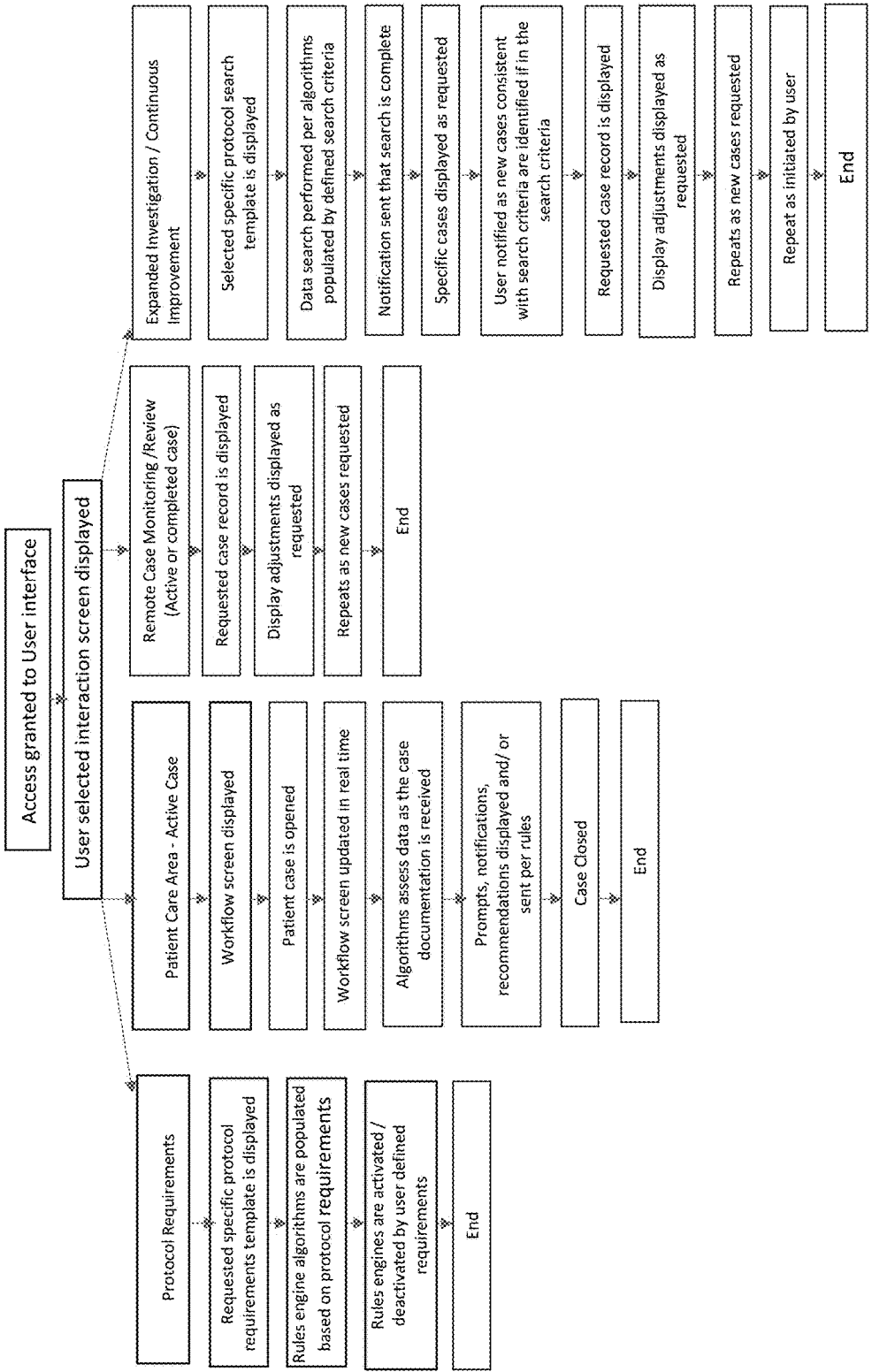
FIG. 13 is a flow diagram of the user interface rules engine of the continuous improvement system used with the present invention.

The communication hub acquires and time stamps monitored data elements from any electronic device, including medical devices, monitoring and/or treating a patient and translates and transmits the monitoring data over a network to a storage location to be processed by the interoperability environment engine, which is essentially the user interface rules engine. Monitored data comprises physiological data elements, video data elements, and audio data elements. The data collected is synchronized using the time of data collection, i.e., the time stamped monitored data elements. Even if the data already has some sort of time stamp, a time stamp is applied because the data collection time synchronization is required to eliminate the need to collect the internal clock times of the electronic devices providing the data. This is critical because the internal clocks of the electronic devices are not always synchronized with each other. The system communicates, agnostically, with any electronic device including medical devices and manually entered data. As seen in FIGS. 12 and 13, the system identifies which information is actionable using an algorithm based upon user criteria. The term agnostic or agnostically is intended to mean that, when data is collected, it can be collected from any electronic device, especially medical devices, regardless of the computer language in which the device operates. Where there are differences, the language can be translated. This allows for an ability to gather data from a greater variety of electronic devices.

Time stamping software for time stamping data is known in the art and can be employed for such purpose. In the present invention, the data is time stamped, as the data is collected and stored in the communication hub. Time stamping prior to storage provides a means to ensure that the data collection time is maintained if the data cannot be transferred to the data storage. Since all communication hubs are time synchronized, regardless of the data source, the time of data collection is used to organize the data within the data repository. Therefore, time stamping of the data provides a means to overlap the data providing an accurate representation of the various patient care interactions and the patient response to these interactions. This provides the process of time stamping for each source of data as it is collected agnostically from the device and is unique in the ecosystem of the present invention.

An interoperability environment is represented in FIG. 1, which is a block diagram of a global interoperability environment. At the center of FIG. 1 is the interoperability environment engine 101, referred to as the engine. This is to symbolize that it is the core communication tool to ensure timely and accurate communication between the various sources and targets of the data being collected and shared in the global environment. As noted by the two-way arrows, the present invention also supports communication between any number of locations with connections to the interoperability engine.

The interoperability environment is also composed of an ecosystem 102. The ecosystem (which can also be referred to as ECO System) is composed of any number of hardware options, utilizing various operating systems such as Linux, Windows, and MacOS. The ecosystem resides in close proximity of the electronic devices, including electronic medical devices (or EMD) 106, talking with the ecosystem, via any number of communication channels including LAN, Serial, Wi Fi, wireless, etc. The ecosystem is utilized as the conduit between the medical devices and the engine to collect, translate and transfer electronic data to the engine for processing to the proper storage locations or specific data targets.

The interoperability environment engine includes a data storage engine and has one or more data repositories to store all data collected prior to sending the data to any target location. For example, the data can come from the patient 100, electronic medical devices 106, workstations 107, patient record data storage 103, remote displays 108, remote access devices 109, mobile devices 110, reference materials 111, internet links 112, and the like. The data storage engine is a software module that a database management system uses to create, read, and update data from a database. The engine tracks each data field based on a start date and end date of the parameter being collected. When combined with the engine time stamping and data collecting, the interoperability environment is capable of supporting data analysis of individual parameters as well as interactions with other parameters. Patient Record Data Storage 103 contains all required patient care data collected and stored by the engine.

The data storage engine can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language.

As can be seen in FIG. 12, data from various sources, including monitored data elements from any electronic device, such as medical devices for monitoring and/or treating a patient, and which is essential for the user interface rules engine, is received. Monitored data can comprise physiological data elements, video data elements, and audio data elements. Once the data is received, it is date stamped, and stored. The data which needs to be translated or converted to the machine-language of the communications hub of the present invention, is translated. If translation is unnecessary, the data is stored, preferably in a cloud storage, which provides remote access to the data. The data is then evaluated for the accuracy of the data and that is verified. In response to a request for data transfer to a target device, the applicable data is collected per the data mapping requirements. If data translation is needed for the target device, evaluation and translation are done. Then, the data is transmitted to the target device and the accuracy is verified.

The communication hub acquires and time stamps monitored data elements from any electronic device, including medical devices, monitoring and/or treating a patient and translates and transmits the monitoring data over a network to a storage location to be processed by the interoperability environment engine, which is essentially the user interface rules engine. Monitored data comprises physiological data elements, video data elements, and audio data elements. The data collected is synchronized using the time of data collection, i.e., the time stamped monitored data elements. Even if the data already has some sort of time stamp, a time stamp is applied because the data collection time synchronization is required to eliminate the need to collect the internal clock times of the electronic devices providing the data. This is critical because the internal clocks of the electronic devices are not always synchronized with each other.

Time stamping software for time stamping data is known in the art and can be employed for such purpose. In the present invention, the data is time stamped, as the data is collected and stored in the communication hub. Time stamping prior to storage provides a means to ensure that the data collection time is maintained if the data cannot be transferred to the data storage. Since all communication hubs are time synchronized, regardless of the data source, the time of data collection is used to organize the data within the data repository. Therefore, time stamping of the data provides a means to overlap the data providing an accurate representation of the various patient care interactions and the patient response to these interactions. This provides the process of time stamping for each source of data as it is collected agnostically from the device is unique to the ecosystem today.

The novel process improvement tool enables collection, storage and automation of process controls and/or workflows on vast disparate data streams that normally are not accessible with paper records or poorly accessible due to isolated ancillary data systems with current electronic systems. Workflow automation changes and data points collected can be easily augmented. The improvement tool of the present invention gives users unique ability to dynamically organize data into views of patient populations regardless of geographic location, with additional ability to pare view according to user specified criteria and the ability to collect data from devices, HIT systems, external sources, user input, or any other source of data which can be made available in electronic format.

The data entry can be a mix of automated and user input. The present invention has the ability to use any of the above to create a set of evaluations on the data stream to trigger notifications intended to notify about deviations from expected workflow, process control or clinical course, as well as the ability to review and replay the sequence of data points in the past so that users can engage in a critical evaluation of a specific event or sequence of events that led to a negative clinical outcome, or non-compliance with or failure of a process control or workflow. The present invention has the ability to use historical data to generate guidance to manage clinical conditions or new process controls/workflows in real time and the ability for a user to acknowledge that a clinical guidance was true/valid in real time.

The present invention has the ability to change execution pathway per user criteria depending on inputs in real time (e.g. data from a micro assessment could change the frequency of future assessments etc.), as well as enable end-users who are consuming the notifications of the improvement tool to direct and coordinate the team to change the input provided to the improvement tool at the time of the review of data so that the any updated workflow, for instance with additional evaluations, or modified evaluations.

The present invention has the ability to collect, store, and process data in real time. It can compose views that organize data for end-users to consume, to let the user create execution steps on the data streams, to notify end-users based on execution steps defined by end-users, and to present an organized view of data within a timeline of events. Further, the present invention has the ability for end-users to change or augment the execution steps and notifications at the same time the end-user is reviewing data.

The remote view system can include software means to review remotely all applicable data associated with the patient current condition, treatment and history to determine appropriate recommended patient care, means to define specific notification rules to define when to provide notification to any number of individuals required to be notified when the defined condition is met, means to allow persons to access to their personal schedule and/or the schedule of their subordinates, a dashboard to identify specific care areas, or patients of potential interest based on defined rules, means to review adherence to patient care plan and the patient's response to the treatment may be reviewed remotely with real time data, and means to select any point in time associated with the patient record to assess patient response before and/or after that point in time.

The interface rules engine creates guidance rules one the end-user defines the criteria to be evaluated and the notifications that need to be delivered to the care team. End-user can define criteria based on any data-point available in the collected data stream, e.g., from medical devices. Users can be clustered into groups. Patients can be clustered into groups. Patients can be "tagged" with user defined criteria. Patients can be stratified according to user defined criteria in real time. Certain thresholds can be altered by an end user on the fly.

The remote device 12 can include any number of exemplar devices. Such exemplar devices include, but are not limited to, a mobile phone, a Smartphone, a personal digital assistant (PDA), a laptop, a tablet personal computer (PC), a desktop PC, and/or combinations thereof. The remote device 12 includes a display 22, a processor 24, memory 26, an input interface 28, and a communication interface 30. The processor 24 can process instructions for execution of implementations of the present disclosure. The instructions can include, but are not limited to, instructions stored in the memory 26 to display graphical information on the display 22. Exemplar displays include, but are not limited to, a thin-film-transistor (TFT) liquid crystal display (LCD), or an organic light emitting diode (OLED) display.

The memory 26 stores information within the remote device 12. In some implementations, the memory 26 can include a volatile memory unit or units, and/or a non-volatile memory unit or units. In other implementations, removable memory can be provided, and can include, but is not limited to, a memory card. Exemplar memory cards can include, but are not limited to, a secure digital (SD) memory card, a mini-SD memory card, a USB stick, and the like.

The input interface 28 can include, but is not limited to, a keyboard, a touchscreen, a mouse, a trackball, a microphone, a touchpad, and/or combinations thereof. In some implementations, an audio codec (not shown) can be provided, which receives audible input from a user or other source through a microphone, and converts the audible input to usable digital information. The audio codec can generate audible sound, such as through a speaker that is provided with the remote device 12. Such sound may include, but is not limited to, Sound from Voice telephone calls, recorded Sound (e.g., voice messages, music files, etc.), and Sound generated by applications operating on the remote device 12.

The remote device 12 may communicate wirelessly through the communication interface(s) 14, which can include digital signal processing circuitry. The communication interface(s) 14 may provide communications under various modes or protocols including, but not limited to, GSM voice calls, SMS, EMS or MMS messaging, CDMA, TDMA, PDC, WCDMA, CDMA2000, and/or GPRS. Such communication may occur, for example, through a radio-frequency transceiver (not shown). Further, the remote device can be capable of short-range communication using features including, but not limited to, Bluetooth and/or Wi-Fi transceivers (not shown).

The remote device 12 communicates with the network 16 through the connectivity interface(s) 14. The connectivity interface(s) 14 can include, but is not limited to, a satellite receiver, cellular network, a Bluetooth system, a Wi-Fi system (e.g., 802.X), a cable modem, a DSL/dial-up interface, and/or a private branch exchange (PBX) system. Each of these connectivity interfaces 14 enables data to be transmitted to/from the network 16. The network 16 can be provided as a local area network (LAN), a wide area network (WAN), a wireless LAN (WLAN), a metropolitan area network (MAN), a personal area network (PAN), the Internet, and/or combinations thereof.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

Figure 2:
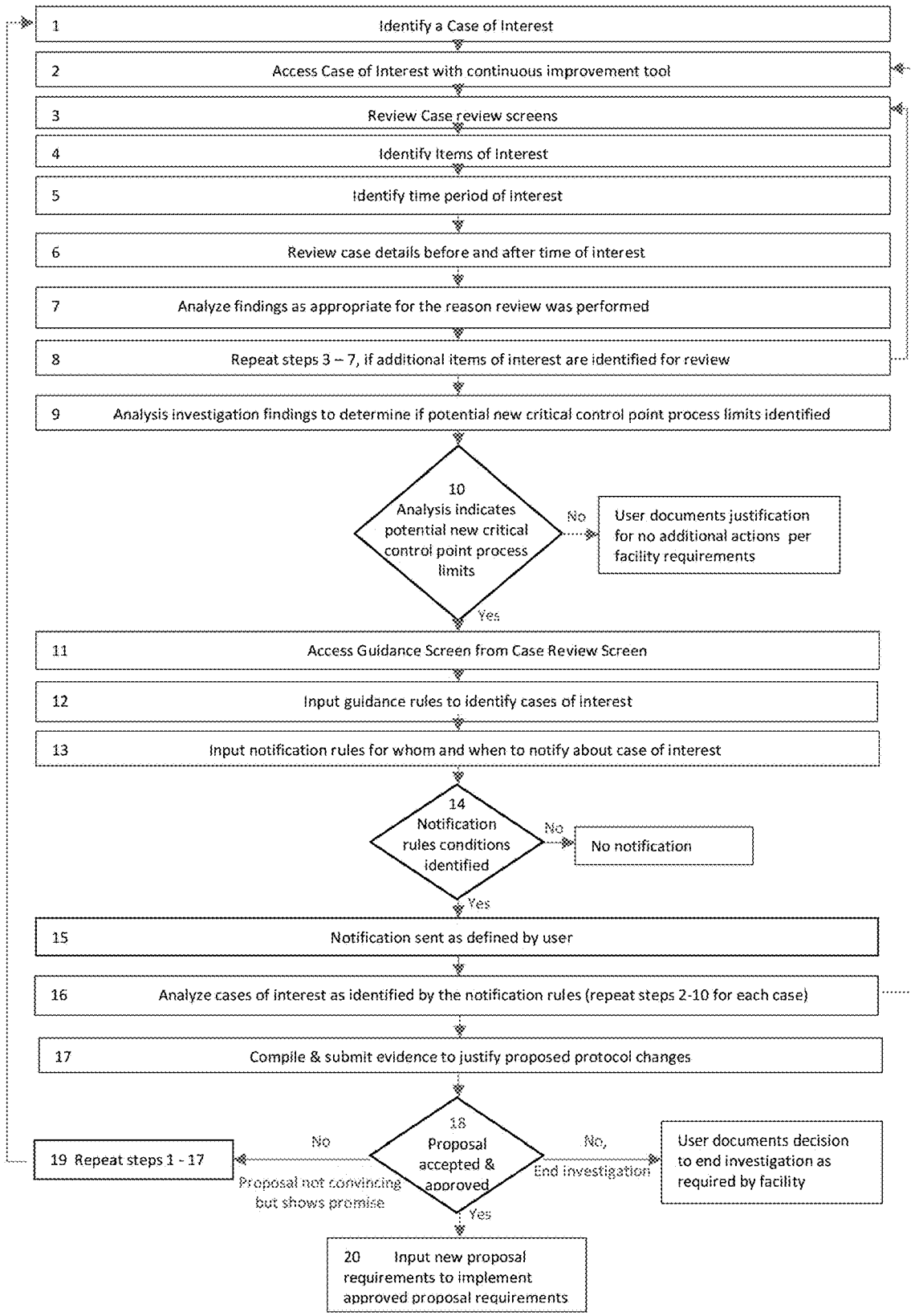
FIG. 2 illustrates the flow of a decision support algorithm in accordance with the present invention.

FIG. 2 is a flow diagram of the use of the remote view playback system of the present invention. The use could, for example, be the use for an anesthesia protocol illustrated in FIGS. 3-10. In that process, a case is identified and accessed. The case is reviewed while identifying items and time periods of interest to access the details of the case required to assess the status of the patient during the active case to determine the appropriate course of action for the patient. The real benefit of the remote view here is that the practitioner has access to details not previously available from a remote access point. Additionally, the data available in remote view provides the practitioner the ability to access data that is not available at the point of care. (Historical data is not available from active patient monitors.).

The present invention allows a clinician to view permanently saved waveforms and physiologic data values from a central location. For example, if a waveform and physiologic data may need to be reviewed and signed by a clinician. Once the waveform and physiologic data has been signed, it is stored permanently in the historical queue.

The present invention allows for waveform data to viewed on any remote screen, including personal computers, tablets, smart phones, intelligent workstations, and the like. Upon request, the waveform of data related to the patient care record can be displayed, along with any additional quality data desired. The waveform replay would be available at any time after the data is stored. While displayed, any time point in the case being reviewed will be available.

For example, when selecting any time point in the case for review, the waveform data will be available along with other data that is part of the patient care record such as the following:

i. Pre-procedure evaluation
ii. Procedural steps taken thus far
  1. Intubation
  2. IV placement
  3. Anesthesia started
  4. Incision
  5. Etc.
iii. Practitioner documented evaluations
iv. Medical device data including patient vital sign monitors.
v. Drug/fluid delivery details
  a. Time (delivered or start, change and end)
  b. Quantity
  c. Changes in delivery, etc.
vi. Supportive data from various data sources including
  a. Labs
  b. Blood bank
  c. Patient medical history
  d. Pharmacy The time selecting unit may include a cursor to select coordinate positions by allowing a user to move and position the cursor, and a cursor monitoring unit to acquire a time corresponding to the cursor's coordinate position while the cursor moves. The apparatus may further include a time display unit to display a time acquired by the cursor monitoring unit in the trend display graph.

The system further includes a data storage unit to store the measurement values of and waveforms of the physiological parameters The following terms used in the description that follows. The definitions are provided for clarity of understanding:

Assessment data—assessment data is all data relevant to the health of a patient.

Healthcare location—A "healthcare location;" a facility, whether temporary or permanent, that is not generally equipped to provide expert medical care on a twenty-four basis. By way of illustration and not as a limitation, a healthcare location may be a remote clinic, a doctor's office, a field hospital, a disaster aid station, a patient transport vehicle and similar care facilities Caregiver—an individual providing care to a patient. Examples include a nurse, a doctor, medical specialist (for example and without limitation an intensivist, cardiologist or other similar medical specialist).

Clinical data—data relating to the observed symptoms of a medical condition.

Monitored patient—a person admitted to a healthcare location.

Monitored data—data received from monitoring devices connected to a monitored patient. monitored patient—a monitored patient from whom monitored data is collected and whose condition is subject to continuous real-time assessment from a remote command center.

patient data—data relating to a patient's diagnosis, prescriptions, history, condition, laboratory results and other health-relevant data.

Physiological data—any data relating to the functions of the human body and its processes. symptom—any sign or indication of a health condition that can be identified from patient reports and/or assessment data.

The present invention uses a telecommunications network to facilitate rules-based care of patients receiving care in a healthcare location. As used herein, a healthcare location may be a remote clinic, a doctor's office, a field hospital, a disaster aid station, a patient transport vehicle and similar care facilities. A patient may be selected for monitoring based on criteria established by the treatment facility. By way of illustration and not as a limitation, a "monitored patient" comprises a critically ill patient, an acutely ill patient, a patient with a specific illness, a patient with serious injuries, and a patient with an uncertain diagnosis.

Patient monitoring equipment acquires monitored data elements from a patient monitoring station and transmits the monitoring data over a network to a remote command center. Monitored data comprises physiological data elements, video data elements, and audio data elements. The remote command center receives the monitoring data from all patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The data available to the remote command center over the network, that is, the monitoring data and the patient data, is collectively referred to as "assessment data."

In the present invention, a monitored patient care system provides care to monitored patients based on the capabilities of the healthcare location. The rules engine, the decision support algorithms, the order writing software facilities, and the continued care software are adapted to the capabilities of the healthcare location based on the application of site assessment rules to the healthcare location. Using the user interface tool the user may select to create or modify protocol requirements. The user enters the protocol requirements into the protocol template. Once accepted, the protocol requirements are loaded into the rules engine. The rules engine monitors the actual protocol parameters against the protocol requirements. Deviations to protocol requirements initiate notification to identified individuals. For example, an anesthesia protocol may require a proactive delivery of antibiotics, if the patient records does not indicate that the antibiotics have been delivered, the system prompts the user to deliver the antibiotic. In the present invention, components of a healthcare location patient care system may be supplied to the healthcare location to improve the level of its treatment capabilities.

Patient monitoring equipment acquires monitored data elements from a patient monitoring station and transmits the monitored data (sometimes also referred to herein as, "monitoring data") over a network to a remote command center. Monitored data comprises physiological data elements, video data elements, and audio data elements. The remote command center receives the monitored data from all patient monitoring stations. The remote command center also accesses other data relating to the condition of a patient. By way of illustration and not as limitation, the remote command center has access to data relating to personal information about the patient (name, address, marital status, age, gender, ethnicity, next of kin), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data") to the extent available from the healthcare location. The data available to the remote command center over the network, that is, the monitored data and the patient data, is collectively referred to as "assessment data."

A rules engine applies a rule or rule set to the data elements selected from the assessment data from each monitored patient to determine whether the rule for that site has been contravened. In the event the rule has been contravened, an alert at the remote command center is triggered. Rules for each monitored patient may be established and changed at the remote command center for each as the patients' conditions warrant. In one embodiment of the present invention, a rule is established to determine whether a patient's condition is deteriorating. An alert that a rule has been contravened comprises advice on treatment of the patient.

A patient rules generator establishes one or more rules for the monitored patient associated with a patient monitoring station. The patient rules generator collects rules performance measures indicative of the ability of the rule to predict changes in the condition of a patient and uses these measures to assess the efficacy of the rule. The patient rules generator may update a rule, determine that a rule is acceptable as is, or determine that there is insufficient data to revise a rule.

The patient rules generator may also evaluate the assessment data of patients with similar conditions to determine whether a predictive rule can be written and applied to patients with the same or similar conditions. The patient rules generator may also test a proposed rule against historical data to determine whether the rule is predictive of a change in a patient's condition. The patient rules generator generates a rule that is consistent with the service level measures established by a site assessment module.

FIG. 13 is a flow diagram illustrating the use of the user interface rules engine. A user may enter and exit the user interface as they want. Once a user is granted access, a user selected interaction screen is displayed. These can include protocol requirements, patient care for an active case, remote case monitoring or review of an active or completed case, or an expanded investigation or continued improvement investigation. Noted below are examples of the user completing specific activities before logging out and then logging in the next activity. Only system activities are included. A user initiates an action prior to the system responding.

Example 1, to review or create Protocol Requirements:
    User interface access is granted
    Requested specific protocol requirements template is displayed
    Rules engine algorithms are populated based on protocol requirements
    Rules engines are activated or deactivated by user defined requirements
    The process is Ended.

Example 2, a Case Process:
    User interface access granted
    Workflow screen displayed
    Patient case is opened
    Workflow screen updated in real time
    Algorithms assess data as the case as documentation is received
    Prompts, notifications, recommendations displayed or sent
    Case closes
    End.

Example 3, Case Review (Active or completed):
    User interface access granted
    Requested case record is displayed
    Display adjustments displayed as requested
    End.

Example 4, Expanded Investigation/continuous improvement (After initial case review):
    User interface access granted Selected specific protocol search template is displayed Data search performed per algorithms populated by defined search criteria Notification sent that search is complete Specific cases displayed as requested User notified as new cases consistent with search criteria are identified if in the search criteria See Case Review Repeat as initiated by user.

For the purposes of remote view, only the portion of the flow diagram associated with review of active case is relevant. Remote view provides the user the ability to review from their current location. The user has the ability to access all relevant data collected during the active case. This provides the user with the ability to assess the state of the patient based on a level of detail not currently available to the user. FIG. 3-10 provide examples of details available while using the remote view capabilities during an active case.

The present invention provides continued care software that uses elements of the assessment data to provide decision support and that prompts a user for input to provide decision support to caregivers. A decision support algorithm responds to elements of assessment data to produce textural material describing a medical condition, scientific treatments and possible complications. This information is available in real time to assist in all types of clinical decisions from diagnosis to treatment to triage.

In the present invention, patient-monitoring equipment acquires monitored data elements from a patient monitoring station and stores monitoring data locally. The stored monitoring data is sent to a remote access point along with patient data at a pre-established time or when requested by remote access point. The remote command center evaluates the "delay" monitored data and assessment data in the same manner as if these data were received in real time. By way of illustration, the remote command center will apply the rules engine and the decision support algorithms to the delayed monitored data and patient data and provide guidance to the healthcare location. The present invention thus provides high quality care in environments where continuous high bandwidth communications are not available or economically infeasible.

The system of the present invention collects the data and stores the data. The patient record in the medical facility electronic medical record system (EMR) contains the same information as is known in the art with other systems. The EMR is one target and receives only the data required by the specific target. The data sent to the EMR plus any other data collected is stored in the cloud and filed support the assessment of the case. There is the ability to store some of the data as case record and other additional data collected in the Quality data. The potential claims being addressed here is another example of how we continue to add functionality and features by finding new ways to more fully leverage the knowledge we are gaining as we gain knowledge. This is a perfect example of how the system has the ability to grow as new knowledge is gained.

The invention is capable of collecting any identified data at a frequency that supports a meaningful assessment of patient interactions and patient response to those interactions. The term data includes but is not limited to patient medical history, patient interaction details including person performing the interaction, the time provided, any drug, disposable or medical device used to complete the interaction, numeric patient vital signs provided by active patient monitors, Waveforms provided by active patient monitors, changes to settings of any medical device used on the patient, lab results, practitioner notes and documented observations.

The invention is capable of displaying the information along a timeline of the treatment period. The display may be configured to provide a graphical representation of any numeric patient vital sign collected during the treatment. Additionally, the invention supports the viewing of the waveform data generated during the treatment as an accurate representation of the waveform screens on the active patient monitors.

Using the review screen the user may select any specific time on the timeline to review the patient vital signs values at that time. With respect to numeric and waveform data the system has the ability to move forward and backward during the treatment to assess potential link between patient interaction and patient response.

Using these tools, the user has the ability to fully assess the status of the patient and based on details reviewed during the case history, assess the patient's responses to the patient care delivered. Based on the user assessment, the user may determine there is a need to modify the patient care plan or to take actions to return to the originally planned care. Without access to the historical date displayed in waveform, numeric, image and textual format the user does not have access to fully assess the situation.

The present invention supports the ability to move back in time during the current patient care under review. The same screens may also be utilized to evaluate the case during formal reviews. These screens also include icons to show when specific patient interactions were performed.

The waveform data is collected directly from the medical devices. These waveforms are stored with the patient records and/or quality records. Once stored the waveforms may be displayed and played. With the ability to play the stored waveforms the system is also includes to play, replay, fast forward or fast reverse to identify the time periods of most interest to the medical practitioner reviewing these records.

Example of the Remote View Tool:

Remote view supports telemedicine by providing the remote practitioner with real time access the patient's record and ability to review all vital signs, patient care activities and patient response to the treatment leading up to the current condition. This provides for a more complete understanding of the patient condition. An example of this is as Anesthesiologist supervising multiple CRNAs. Remote view provides the supervisor to review the facts regarding a specific patient while walking to the OR to assist the CRNA. Thus, reducing the time required to review the patient status with the CRNA prior to taking the appropriate actions to address the situation.

The system of the present invention will best be used when there is a specific reason to analyze the details of the patient's condition remotely. Examples include: providing physicians with the ability to: check up on their patients remotely, improve support of attending practitioners under their supervision, prioritize their schedules based on the current condition of their patients, and provide remote telemedicine intensivists the ability to review events leading up to the current patient condition.

FIGS. 3-12 provide an example for an anesthesia protocol. However, the example and its slides and explanation of each screen are not intended to limit the scope of the capabilities of a continuous improvement system. The system may be configured to support any number of processes.

Figure 3:
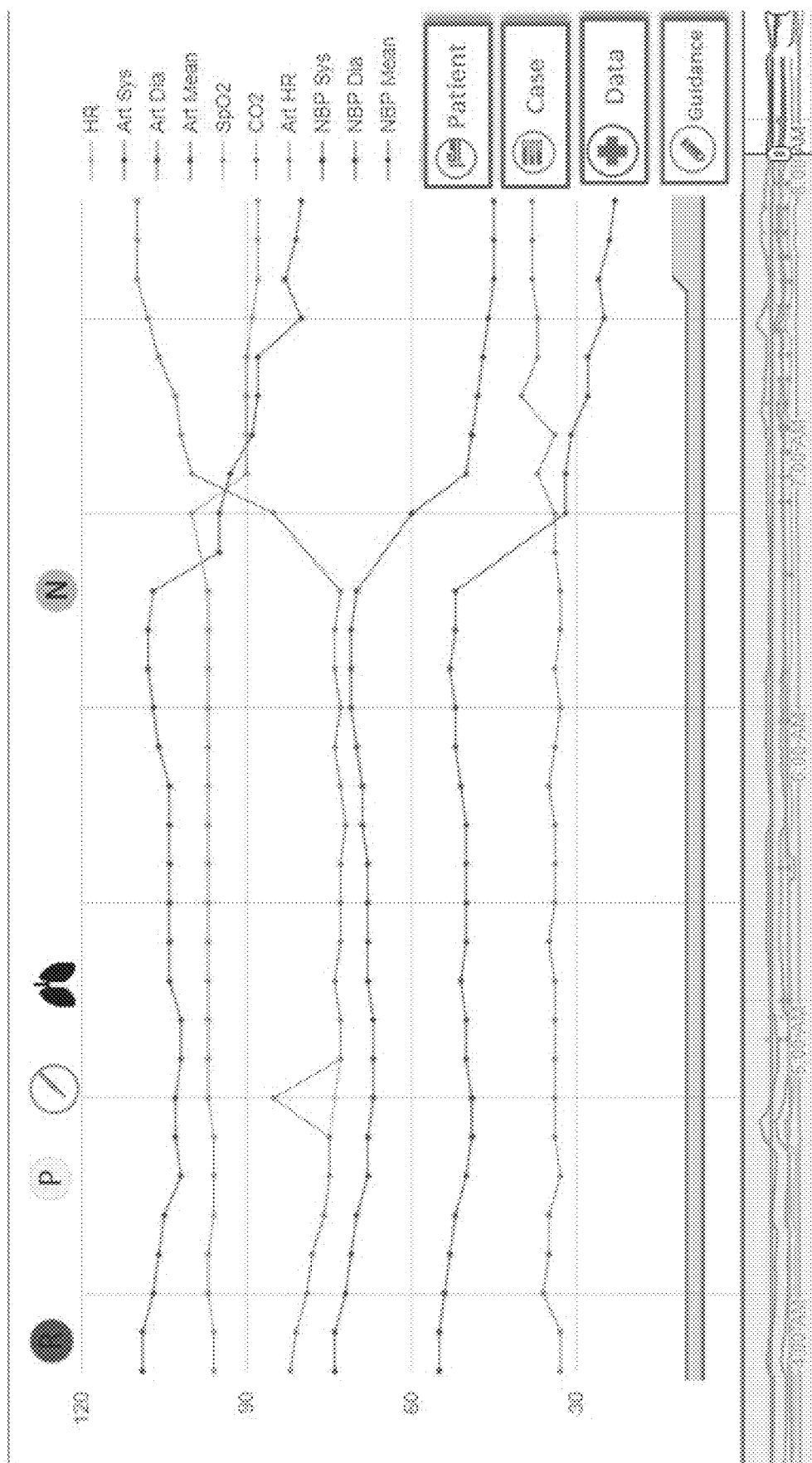
FIG. 3 is a screen shot showing a case analysis review screen.
Figure 4:
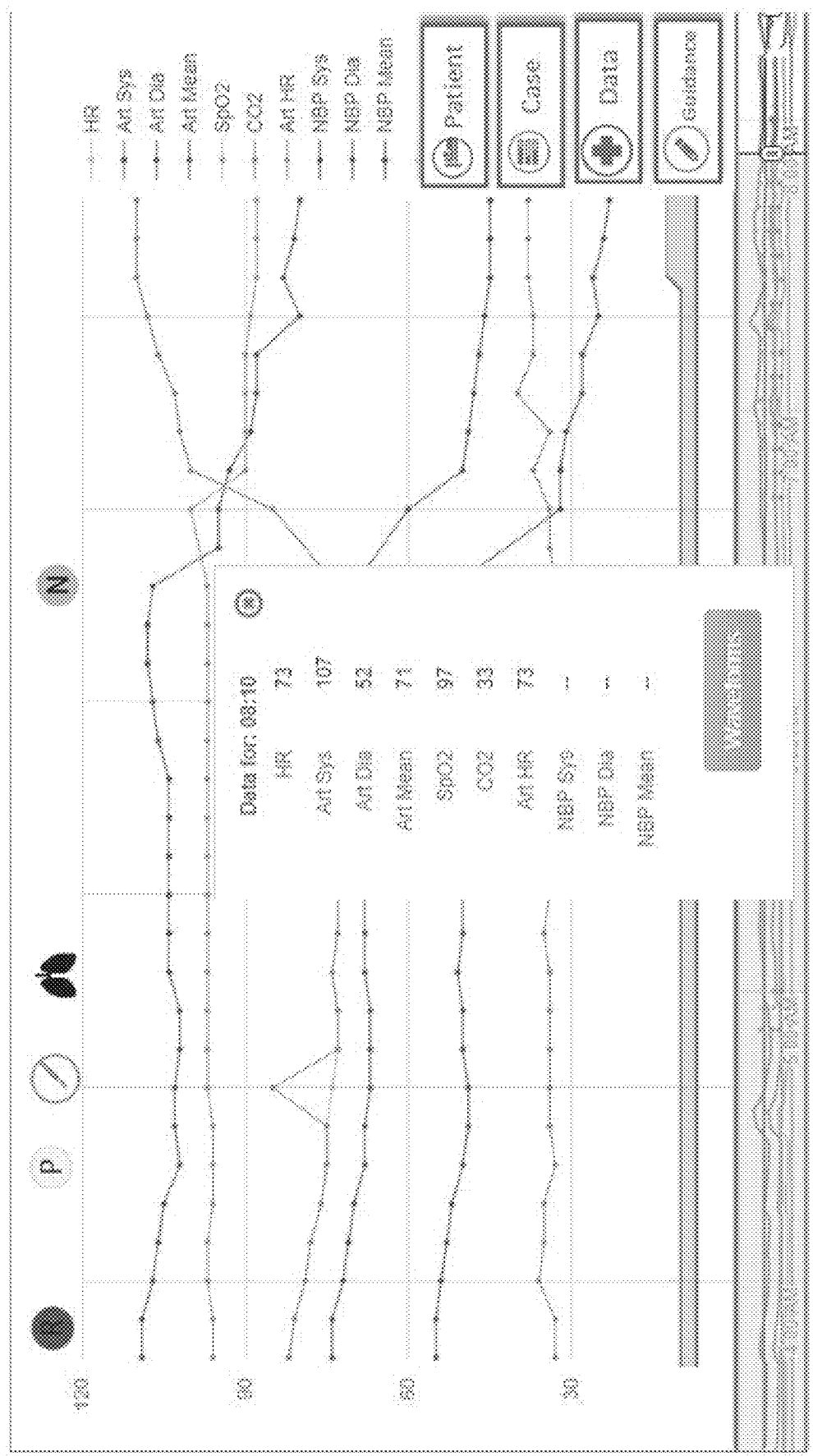
FIG. 4 is a screen shot showing a case analysis review screen showing interaction with data options.
Figure 5:
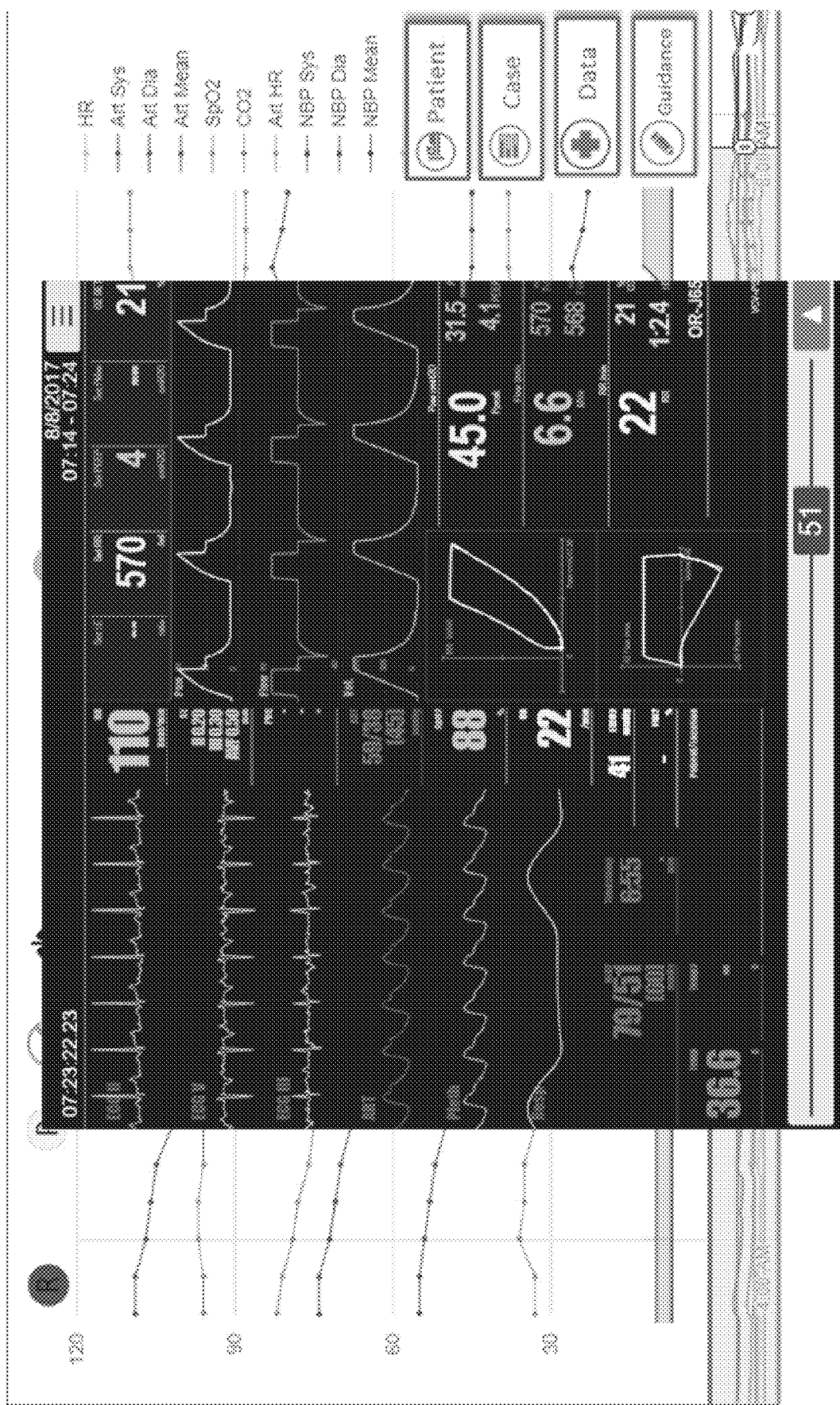
FIG. 5 is a screen shot showing a case analysis review screen which includes waveform displays.
Figure 6:
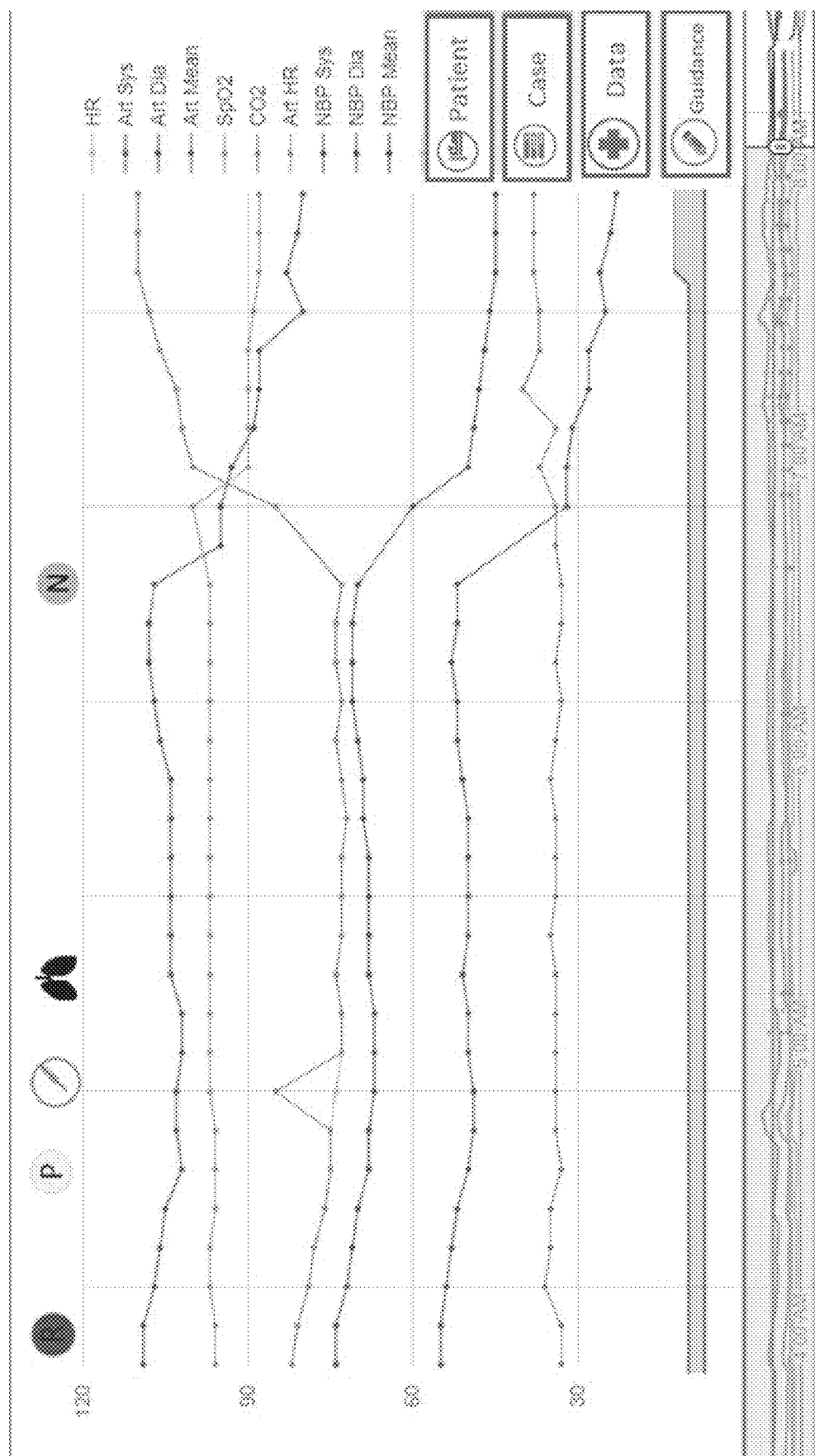
FIG. 6 is a screen shot showing a case analysis review screen showing a guidance tool to create or modify a guidance.

In the present example of a case analysis, a review screen is provided that provides on overview of the case including, but not limited to:

Graphical representation of the patient vital signs during the case, including icons indicating when specific interaction with patient occur
Legend of the graphs
Drug delivery
Incision
Ventilation
Case Detail Selection Keys
Patient—details
Case
Data
Guidance The screenshots provided walk through an example where data collected through a case is reviewed. In the timeline, data from multiple sources is visible along with clinical events, (i.e. incision) The screenshots FIGS. 3, 4, and 5 show how clinicians interactively review data along with the guidance editor. Then can evaluate their current process controls (FIG. 6) and make changes to processes based on the review of the case. The screenshots show an example of how this happens. For example, during a review, clinicians might identify that the data shown in the screens of the review tool might be more effective if it also showed data available from cerebral oximetry. Because the platform supports Cerebral monitors, clinicians can request to include cerebral oximeters in the data set collected, so that clinicians can review and use its data to create more effective guidance. The remote view is not limited to the EMR data, the EMR contains a subset of the data available for remote view analysis.

FIG. 3 is a screen shot of a review screen showing an interaction with the review screen data options, including an ability to move the cursor to a specific time in the case and clicks to see specific data details. This screen shot displays the actual collected data at the requested time of the case.

To see waveforms the user clicks on the waveform key, as shown in the screen shot in FIG. 4 and the waveform data collected is displayed as shown in the screen shot in FIG. 5. As seen in the screen shot is FIG. 6, there is a slide at the bottom of the waveform display, which enables the user to move the time back or forward to review changes before or after the selected time. The screen shots illustrate how, from the review screen the user can access the guidance tool which walks the user through the process to create or modify a guidance.

Figure 7:
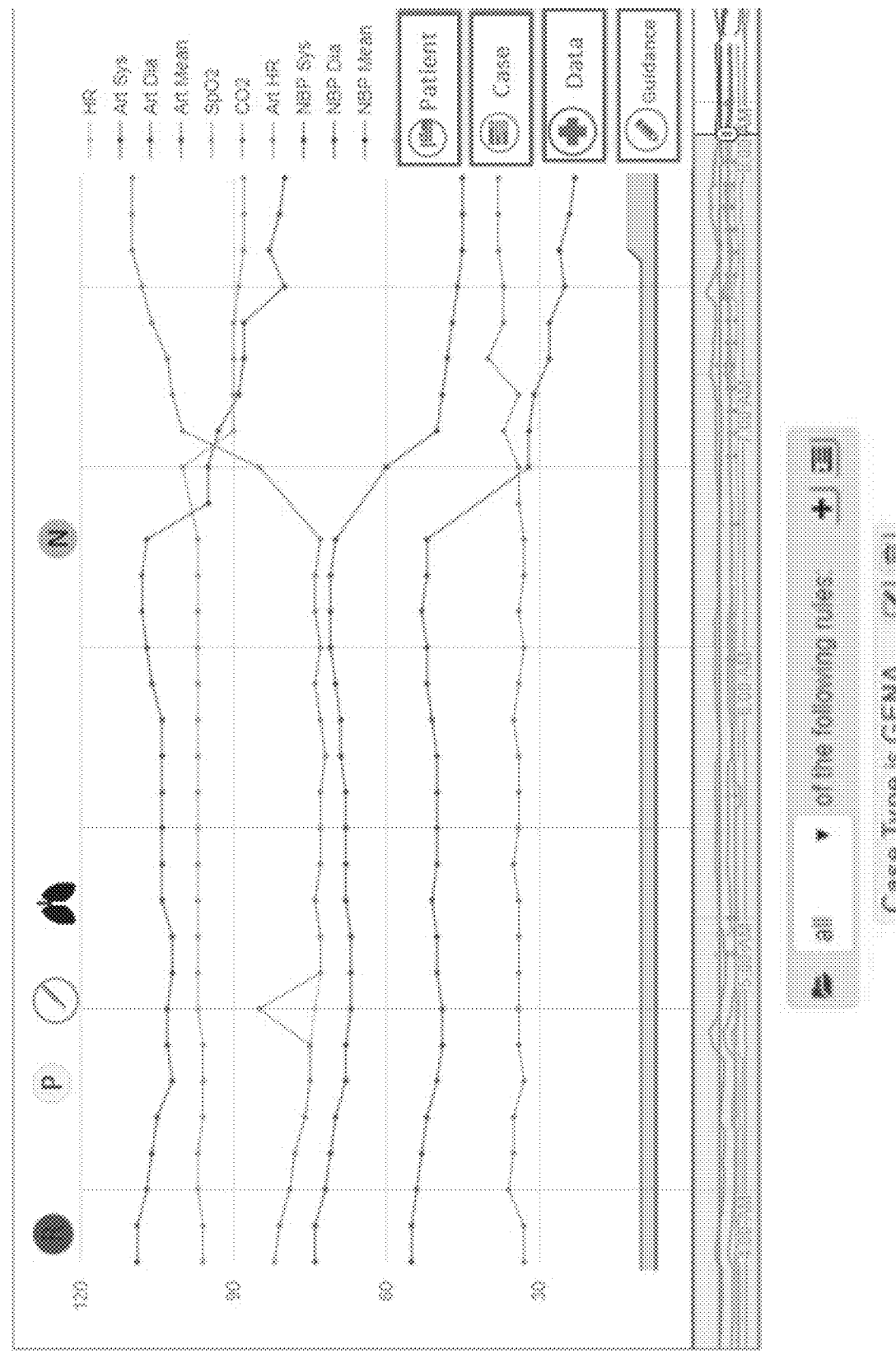
FIG. 7 is a screen shot showing a case analysis review screen showing the selection of a primary filter.

FIG. 7 shows the review screen and the selection of the scope of the primary filter which in this case defines the case type a GENA.

Figure 8:
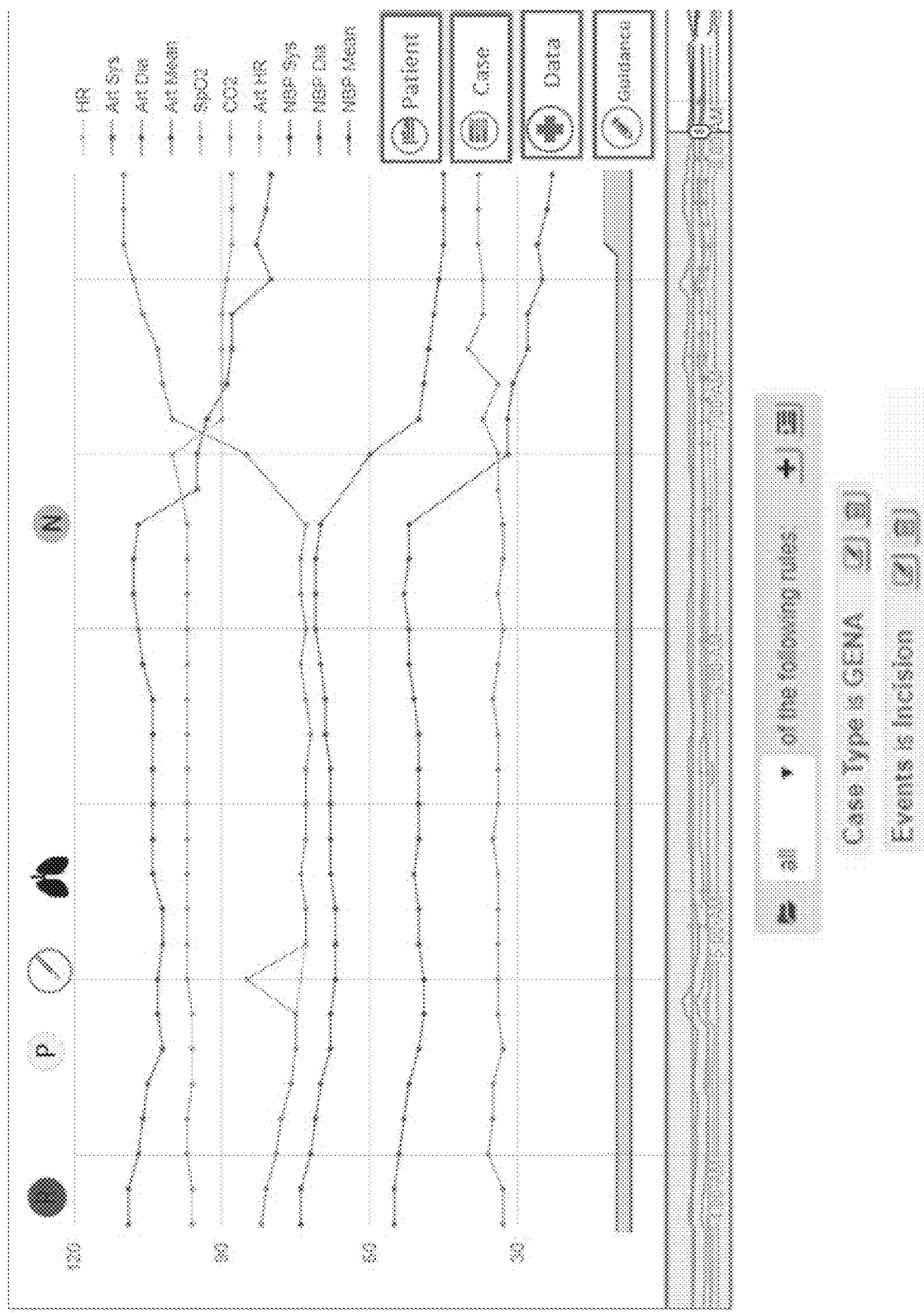
FIG. 8 is a screen shot showing a case analysis review screen indicating that the event is an incision.

FIG. 8 shows the review screen and patient interactions, as well as showing that the event is an incision.

Figure 9:
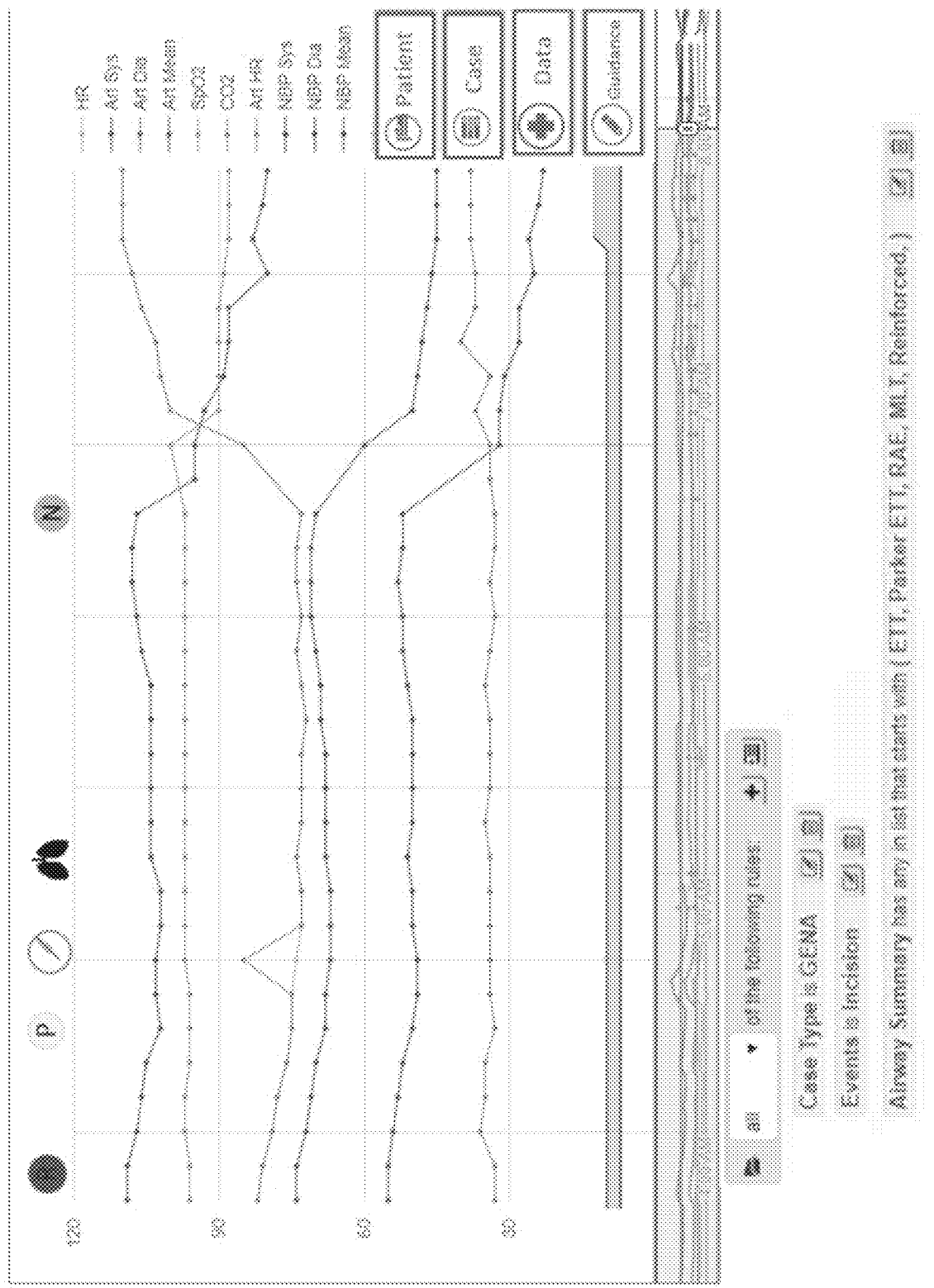
FIG. 9 is a screen shot showing a case analysis review screen which provides an airway summary.

FIG. 9 shows a screen shot of an airway summary and has any list that starts with ETT, Parker ETT, RAE, and MLT and/or reinforced.

Figure 10:
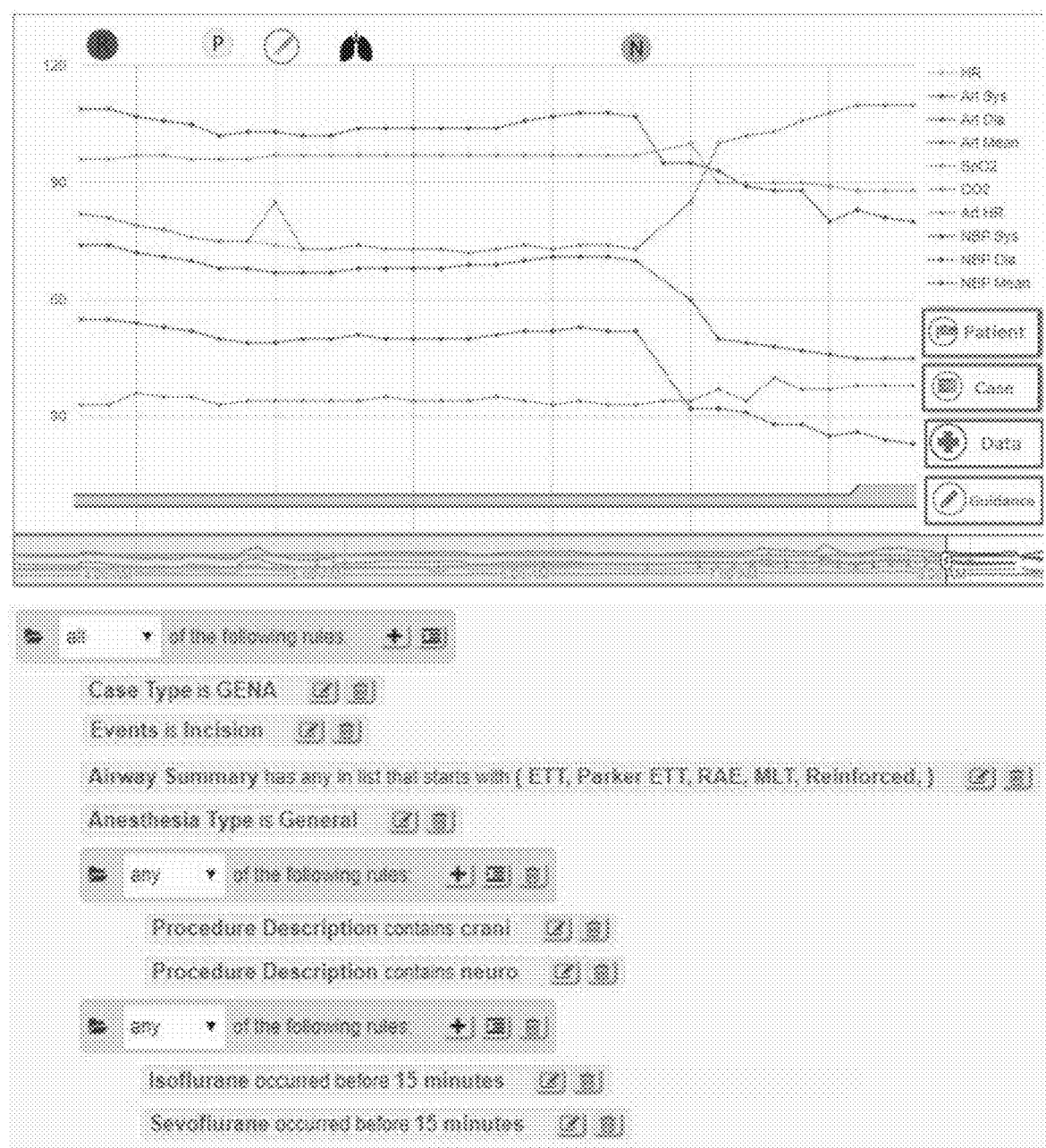
FIG. 10 is a screen shot showing a case analysis review screen showing that the anesthesia is general, as well as the secondary and third level filters.

FIG. 10 shows a screen shot indicating that the anesthesia type is general and defines the scope of secondary filter according to certain rules, including whether the procedure description contains crani and/or the procedure description contains neuro. FIG. 10 also shows the definition of the 3rd level filter, and indicates that Isoflurane occurred before 15 minutes and Sevoflurane occurred before 15 minutes.

Figure 11:
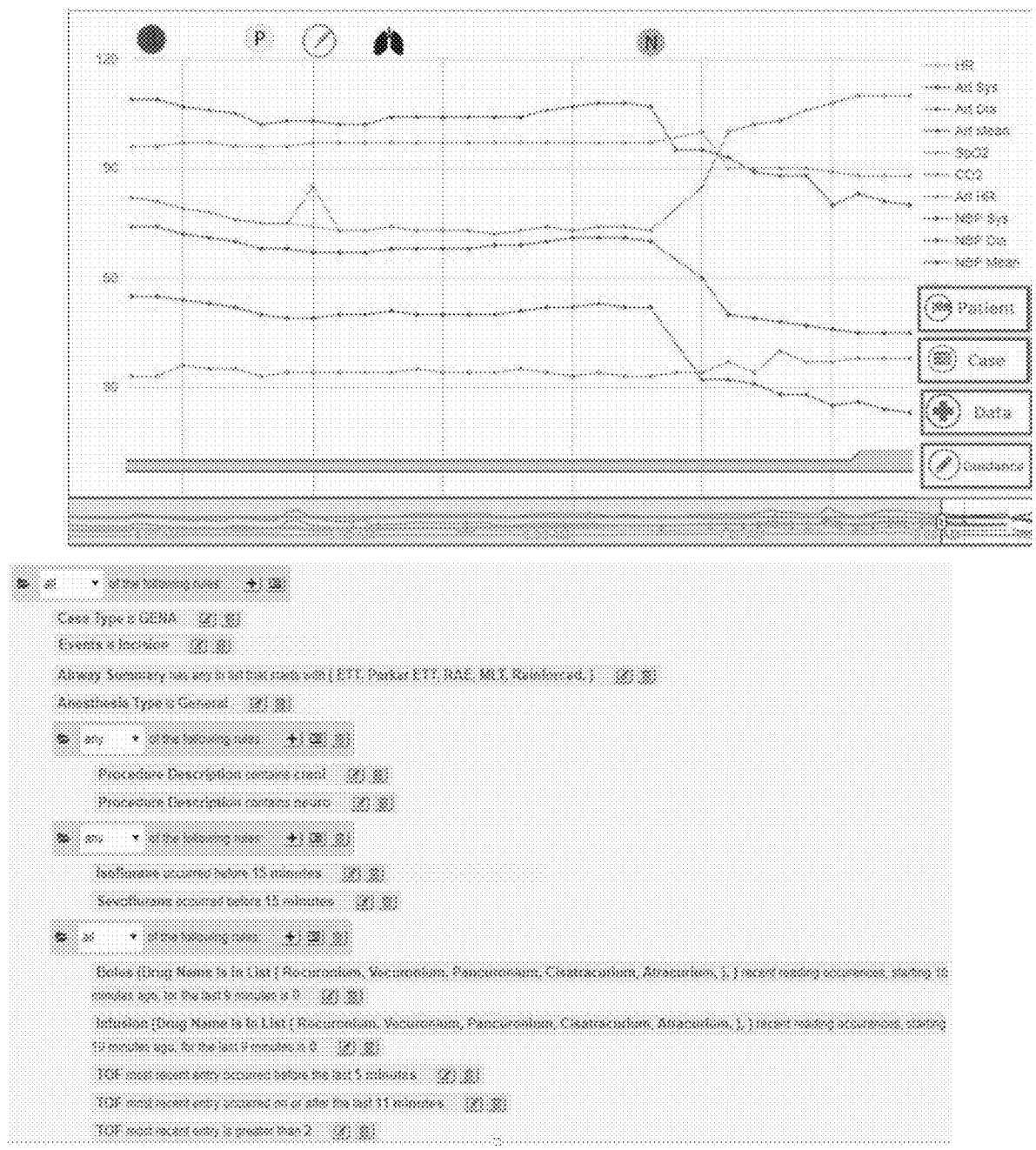
FIG. 11 is a screen shot showing a case analysis review screen which defines the scope of the fourth level filter.

FIG. 11 shows the scope of a 4th level filter as defined by the following rules;

Bolus (Drug Name is in List (Rocuronium, Vecuronium, Pancuronium, Atracurium),) recent reading occurrences starting 10 minutes ago for the last 9 minutes is 0

Infusion (Drug Name is in List (Rocuronium, Vecuronium, Pancuronium, Atracurium),) recent reading occurrences starting 10 minutes ago for the last 9 minutes is 0

TOF most recent entry occurred before the last 5 minutes
TOF most recent entry occurred on or after the last 11 minutes
TOF most recent entry is greater than 2.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated.

What we claim is:

1. A system for handling patient data, comprising:
one or more communication hubs configured to receive data from a plurality of electronic devices corresponding to one or more patients, the data acquired by the plurality of electronic devices in real time, each communication hub having a processor and memory and configured to execute instructions for storing and processing the received data in real time, the processing including transmitting selected portions of the received data to selected ones of the electronic devices and translating the received data to a first machine-language and translating the received data to be sent to a receiving one of the electronic devices from the first machine-language to a second language compatible with the receiving electronic device; and
a remote view system including a user interface rules engine and configured to receive and transmit input data input by a user and to allow the user to review remotely, in real time, the data received with the one or more communication hubs, including applicable data associated with an active case of a patient to determine recommended care for the patient, the applicable data including patient vital signs and waveforms obtained during the active case, the remote view system further configured to allow the user to define specific notification rules to define when to provide notification when a defined condition is met,
the user interface rules engine permitting the user to review the received data within a timeline of events depicting patient interactions for the patient and patient vital signs before and after each patient interaction,
the user interface rules engine being configured to permit the user to review the received data regarding treatment at a selected time and to review the received data corresponding to a time before or after the selected time, wherein the timeline of events is configured to be displayed along with a notification rules generator via which the user can set one or more filters for defining specific notification rules to define when to provide notification when the defined condition is met, the notification rules generator including one or more menus, each menu associated with a respective filter of the one or more filters, the notification rules generator displaying a plurality of user-defined rules for each filter, and each menu including an all selection and an any selection, the all selection dictating that all of the plurality of user-defined rules for that filter be met and the any selection dictating that any of the plurality of user-defined rules for that filter be met, wherein the received data is sorted to generate a health history for each patient based on information regarding identified ones of the electronic devices currently connected to each patient.

2. The system of claim 1, wherein the one or more communication hubs are connected to the remote view system via a communication network.

3. The system of claim 1, wherein, upon occurrence of a predetermined event in regard to the patient, the user interface rules engine is configured to gather the received data corresponding to the patient for a first predetermined time before and a second predetermined time after the predetermined event to generate the timeline of events.

4. The system of claim 3, wherein the predetermined event is detected based on the received data from a patient record corresponding to the first patient.

5. The system of claim 3, wherein the predetermined event is indicated by the user to the user interface rules engine.

6. The system of claim 1, wherein the user interface rules engine defines criteria determining when to communicate that cases meeting the defined criteria are available for review.

7. The system of claim 1, wherein the one or more filters include a primary filter and a secondary filter.

8. The system of claim 7, wherein the one or more menus includes a first menu for the primary filter and a second menu for the secondary filter, wherein, via the first menu, one or more primary notification rules of the specific notification rules can be set and, via the second menu, one or more secondary notification rules of the specific notification rules can be set.

9. A method for handling patient data, comprising:
receiving data, at one or more communication hubs, from a plurality of electronic devices corresponding to one or more patients, the data acquired by the plurality of electronic devices in real time, each communication hub having a processor and memory and configured to execute instructions for storing and processing the received data in real time, the processing including transmitting selected portions of the received data to selected ones of the electronic devices and translating the received data to a first machine-language and translating the received data to be sent to a receiving one of the electronic devices from the first machine-language to a second language compatible with the receiving electronic device;

via a remote view system including a user interface rules engine, receiving and transmitting input data input by a user and allowing the user to review remotely, in real time, the data received with the one or more communication hubs, including applicable data associated with an active case of a patient to determine recommended care for the patient, the applicable data including patient vital signs and waveforms obtained during the active case, the remote view system further configured to allow the user to define specific notification rules to define when to provide notification when a defined condition is met;

permitting the user, via the user interface rules engine, to review the received data within a timeline of events depicting patient interactions for the patient and patient vital signs before and after each patient interaction; and permitting the user, via the user interface rules engine, to review the received data regarding treatment at a selected time and to review the received data corresponding to a time before or after the selected time, wherein the timeline of events is configured to be displayed along with a notification rules generator via which the user can set one or more filters for defining specific notification rules to define when to provide notification when the defined condition is met, the notification rules generator including one or more menus, each menu associated with a respective filter of the one or more filters, the notification rules generator displaying a plurality of user-defined rules for each filter, and each menu including an all selection and an any selection, the all selection dictating that all of the plurality of user-defined rules for that filter be met and the any selection dictating that any of the plurality of user-defined rules for that filter be met, wherein the received data is sorted to generate a health history for each patient based on information regarding identified ones of the electronic devices currently connected to each patient.

* * * * *